United States Patent
Mizutani

(10) Patent No.: US 7,067,712 B2
(45) Date of Patent: Jun. 27, 2006

(54) CASPASE 1 GENE TRANSFER ANIMAL

(75) Inventor: Hitoshi Mizutani, 10-41, Oozono-cho, Tsu-shi, Mie (JP) 514-0046

(73) Assignees: Hitoshi Mizutani, Tsu (JP); Kenji Nakanishi, Takarazuka (JP); Taiho Pharmaceutical Co., Ltd., Tokyo (JP)

( * ) Notice: Subject to any disclaimer, the term of this patent is extended or adjusted under 35 U.S.C. 154(b) by 394 days.

(21) Appl. No.: 10/311,211

(22) PCT Filed: Jun. 15, 2001

(86) PCT No.: PCT/JP01/05110

§ 371 (c)(1),
(2), (4) Date: Dec. 16, 2002

(87) PCT Pub. No.: WO01/95710

PCT Pub. Date: Dec. 20, 2001

(65) Prior Publication Data

US 2003/0159163 A1  Aug. 21, 2003

(30) Foreign Application Priority Data

Jun. 16, 2000  (JP) .............................. 2000-181134

(51) Int. Cl.
- *G01N 33/00* (2006.01)
- *A01K 67/00* (2006.01)
- *A01K 67/027* (2006.01)
- *C12N 15/00* (2006.01)

(52) U.S. Cl. .............................. 800/3; 800/13; 800/18; 800/21; 800/25

(58) Field of Classification Search .................... 800/3, 800/13, 14, 18, 21, 25
See application file for complete search history.

(56) References Cited

OTHER PUBLICATIONS

Musial et al., 1998, Thrombosis Research, vol. 89, p. 253-261.*
Kappel et al., 1992, Current Opinion in Biotechnology, vol. 3, p. 548-553.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
K. Yamanaka et al. Journal of Immunology, vol. 165, pp. 997-1003.
A. Asahi et al. J. Dermatol., vol. 21, pp. 49-58 1999.
S. Wardlow et al. DNA Seq., vol. 10, pp. 133-137 1999.
A. Nasir et al. J. Clin. Invest., vol. 94, pp. 892-898.
P.J. Sansonetti et al. Immunity, vol. 12, pp. 581-590 2000.
Immunology, 1997-98 Published by Nakayama Shoten with partial English translation and its Chemical Abstract 127:246739d.
Clinical Immunology, vol. 30, No. 2, pp. 191-198 1988 with partial English translation.
K. Zepter, et al., Journal of Immunology, vol. 159, No. 12, pp. 6203-6208, XP-002241669, "Induction of Biologically Active IL-1β-Converting Enzyme and Mature IL-1β in Human Keratinocytes by Inflammatory and Immunologic Stimuli", Dec. 15, 1997.

* cited by examiner

*Primary Examiner*—Shin-Lin Chen
(74) *Attorney, Agent, or Firm*—Oblon, Spivak, McClelland, Maier & Neustadt, P.C.

(57) ABSTRACT

A transgenic rodent or its offspring which carries DNA having an exogenous caspase 1 gene integrated thereinto in such a manner as to express the gene specifically to the skin. The transgenic rodent of the present invention spontaneously develops atopic dermatitis in the absence of any specific pathogenic microorganism and is useful as a disease model animal. The transgenic rodent of the present invention is useful for developing preventive and/or therapeutic drugs for atopic dermatitis based on natural immunity and to clarify the onset mechanism of atopic diseases.

12 Claims, 3 Drawing Sheets

CASPASE 1 GENE TRANSFER ANIMAL

TECHNICAL FIELD

The present invention relates to a transgenic animal useful as an animal model for atopic dermatitis.

BACKGROUND ART

Atopic diseases, including atopic dermatitis, asthma, allergic rhinitis, and allergic conjuctivitis, are pathological conditions which permit the subject's own immune system to destroy, and cause disturbance of organs as a result of hyper-responses to environmental antigens to which healthy subjects usually exhibit no response. A conceivable mechanism of development of these diseases includes contribution of Th2 cytokine, which promotes allergic responses. The induction mechanism and regulatory mechanism, which are crucial from the physiological and pharmacological viewpoints, have not yet been completely elucidated.

At present, mainstream treatments of atopic diseases include avoidance of antigens; administration of antihistaminic agents which serve as antagonists against binding of a mediator such as histamine to a receptor; and administration of anti-inflammatory steroids. However, development of improved therapies targeting more specific action mechanisms remains hindered, because no suitable test animals have been provided.

According to conventional techniques, in order to elicit an allergic response from a test animal, the animal must first be sensitized through repeated immunization of an antigen or an allergen in advance, and then be challenged with the same type of antigen or the allergen. Such a process not only imposes considerable workload for simultaneously sensitizing numerous animals, but also produces non-uniformity between animals in terms of reactivity, raising potential problems on reproducibility of the test.

In recent years, NC/Nga mice have attracted attention for their potential use as an animal model of atopic dermatitis. However, this dermatitis is developed only in the case where the host mouse carries a mite, and further, the percent onset is inconsistent and symptoms develop in different forms.

Tests using animals are indispensable in the development of remedies for atopic diseases, and in particular, demand exists for animal models of atopic dermatitis. To date, however, no such animal models of atopic dermatitis having a well-established hereditary background and clarified immunological traits and being available for research and development of remedies and pharmaceuticals under conditions from which specific pathogenic microorganisms are eliminated have ever existed or put into practical use.

Accordingly, an object of the present invention is to create an animal that is useful as an atopic dermatitis model.

DISCLOSURE OF THE INVENTION

In view of the foregoing, the present inventors have focused their research efforts on interleukin 18 (IL-18). IL-18, when processed by a protease called caspase 1 (IL-1β converting enzyme), is transformed from its precursor form to a mature form. The functions of mature IL-18 are known to include: (1) induction of production of IFN-γ, (2) promotion of Fas-mediated apoptosis through facilitated expression of Fas ligand, (3) induction of GM-CSF, and (4) inhibition of IgE production in the co-presence of IL-12. IL-18 is expressed not only in immune tissue but also in a variety of tissues including osteoblast-like stromal cells, keratinocytes, small intestinal epithelial cells, adrenocortical cells, and hypophysis cells, and their physiological roles have been energetically studied (see, for example, Immunology, 1997–98, published by Nakayama Shoten, 62–72; and Clinical Immunology, 30(2), 191–198, 1998). Recently, the present inventors have discovered that over-expression of IL-18, when occurring alone, promotes production of IL-4 and IL-13 and elicits production of IgE. This signifies close interrelation between IL-18 and Th2 cytokine, which relates to the onset of atopic diseases. Therefore, the inventors have considered that if an animal model having enhanced ability in secretion of caspase 1, which converts IL-18 to its mature form, can be created, such an animal would be useful in elucidation of the onset mechanism of atopic diseases and development of therapeutic methods therefor. However, since caspase 1 is an apoptosis-inducing enzyme, simple transfer of a caspase 1 gene for expression in a living body is lethal to the host. Moreover, in order to cause a host to secrete mature IL-18, expression of caspase 1 in cells that produce pro-IL-18 is necessary. Therefore, the inventors have considered that if recombinant DNA engineered so as to express caspase 1 gene specifically in the skin capable of producing pro-IL-18 is transferred to animal cells, the host animal continuously secretes mature IL-18 in blood, and when such an animal is raised under conditions free from specific pathogenic microorganisms such as mites and molds, transgenic animals showing symptoms of atopic dermatitis can be created, thus leading to completion of the invention. In this connection, the present inventors previously studied apoptosis and inflammation due to caspase 1, through direct injection of caspase 1 gene to a healthy mouse, rather than to a fertilized egg thereof (J. Dermatol. Sci. 21(1999): 49–58). However, this mouse did not develop spontaneous inflammation, and thus completely differs from the animal of the present invention.

Thus, the present invention provides a transgenic non-human mammal or its offspring, comprising DNA engineered to contain exogenous caspase 1 gene in such a manner as to be specifically expressed in the skin, and a method for creating the same.

The present invention also provides a method for screening preventive and/or therapeutic substances for atopic dermatitis, characterized by administering a test substance to the mentioned transgenic animal and investigating the ameliorating effect of the substance on atopic dermatitis; and by use of the screening method, to provide a preventive or therapeutic drug for atopic dermatitis which is determined to have ameliorating effect for atopic dermatitis.

BEST MODE FOR CARRYING OUT THE INVENTION

Figure 1:
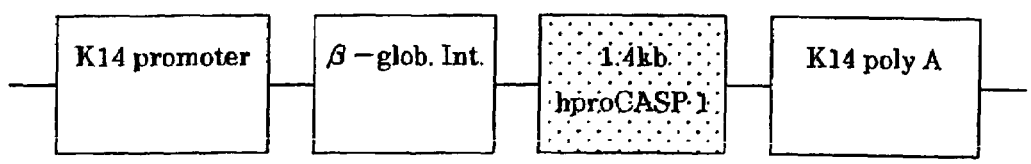
FIG. 1 schematically shows arrangement of components of the recombinant DNA employed in gene transfer.

The somatic cells and germ cells of the transgenic animal of the present invention harbor DNA in which exogenous caspase 1 (CASP1) gene is integrated so that the gene is skin-specifically expressed. The exogenous caspase 1 gene is preferably derived from humans or mice, and examples include human procaspase 1 (hproCASP1) gene, murine procaspase 1 (mproCASP1) gene, human caspase 1 (hCASP1) gene, and murine caspase 1 (mCASP1) gene, with 1.4 kb cDNA of a full coding region of hproCASP1 being particularly preferred.

Preferably, DNA in which the exogenous caspase 1 gene has been integrated so that the gene is skin-specifically expressed is a recombinant DNA containing a exogenous caspase 1 gene and a promoter for skin-specific protein. Examples of the promoter for a skin-specific protein include promoters for proteins which are specifically found in the skin, and specific examples include promoters for keratin 14, keratin 5, keratin 1, keratin 10, and involcrin, with keratin promoters being particularly preferred. The exogenous caspase 1 gene is linked to the downstream of the promoter of the skin-specific protein, and in order to improve expression efficiency of the gene, preferably, an intron, such as β-globin intron, is also linked.

Preferably, the above-mentioned DNA contains a sequence of polyA (usually called a terminator) for terminating transcription of messenger RNA of interest in a transgenic mammal, for enabling manipulation of gene expression by use of gene sequences derived from, for example, viruses and mammals. Preferably, polyA of the aforementioned skin-specific protein is employed, and more preferably, polyA of keratin is employed. In addition, in order to attain enhanced expression of the gene of interest, a splicing signal or an enhancer region of the gene, or a portion of an intron of eukaryotic gene may be ligated to the 5' upstream of the promoter region, between the promoter region and the translational region, or the 3' downstream of the translational region, depending on needs.

Examples of the non-human mammals for transferring the thus-obtained recombinant DNA include cows, pigs, sheep, goats, rabbits, dogs, cats, guinea pigs, hamsters, rats, and mice. Of these mammals, rabbits, dogs, cats, guinea pigs, hamsters, mice, and rats are preferred. Rodentia; in particular, mice, are particularly preferred.

The transgenic animal of the present invention is created by transferring DNA in which the aforementioned exogenous caspase 1 gene has been integrated so that the gene is expressed specifically in the skin to, for example, a fertilized egg of a non-human mammal, and then the egg is implanted into a female individual of the mammal. Preferably, the fertilized egg to be employed is in the period of male pronucleus (approximately 12 hours after fertilization). Examples of techniques for transferring the recombinant DNA include the calcium phosphate method, electric pulse application, lipofection, agglutination, microinjection, the particle gun method, and DEAE-dextran method, with microinjection being particularly preferred.

The fertilized egg to which the recombinant DNA has been incorporated is implanted to a female animal of the same species of the animal from which the egg has been obtained. Preferably, implantation is carried out artificially; i.e., through transplantation and implantation to the oviduct of a pseudopregnant female animal. From the offspring produced by the fertilized-egg-implanted animal, individuals expressing the gene of interest are selected and the selected individuals can be reproduced over generations.

Whether or not the obtained transgenic animal bears the gene of interest can be confirmed by collecting DNA from a skin sample and subjecting the sample to polymerase chain reaction (PCR) and Southern blotting for analysis of the transferred gene.

The thus-obtained transgenic animal of the present invention expresses exogenous caspase 1 gene in the skin, and manifests symptoms of atopic dermatitis even under the absence of a specific pathogenic microorganism. Another characteristic feature of the animal of the present invention is prolonged life span.

The transgenic animal of the present invention has exogenous caspase 1 gene only in the skin. In other words, the exogenous caspase 1 gene is not contained in other tissues of, for example, the liver, kidneys, lungs, brain, or spleen. Thus, the skin of the transgenic animal of the present invention contains mature IL-18 and mature IL-1β. Moreover, the blood of the transgenic animal of the present invention contains both mature IL-18 and mature IL-1β in greater amounts as compared with healthy animals, with the mature IL-18 content being higher relative to mature IL-1β.

The transgenic animal of the present invention develops symptoms of atopic dermatitis—for example, rodent dermatitis, erosive dermatitis, skin ulcer, and erosion—from 8 weeks of age or thereabouts. From 10 weeks of age or thereabouts, observation of skin tissue under an optical microscope will reveal psoriasis-like changes accompanying parakeratosis or other changes such as acanthosisin circumferential thick epidermal portions around ulceration, and the corium of the ulcerate portion is infiltrated with monocytes and mast cells. The keratinocytes of the lesion show acidophilic necrosis which accompanies pycnosis, indicating apoptosis of keratinocytes. Moreover, the transgenic animals created according to the present invention scratch their skin much more frequently than do healthy counterparts, thereby confirming strong itchiness unique to atopic dermatitis. The transgenic animals of the present invention manifest a symptom characteristic to atopic dermatitis; i.e., high blood histamine level and high IgE level.

As described above, since the transgenic animals of the present invention manifest symptoms of atopic dermatitis in the absence of specific pathogenic microorganisms, they are useful as an animal model of atopic dermatitis. That is, administration of a test substance to the transgenic animal of the present invention or its offspring and verification of ameliorating effect on atopic dermatitis enables screening of preventive and/or therapeutic substances for atopic dermatitis. The ameliorating effect on atopic dermatitis may be verified through measurement of blood mature IL-18 level, detection of mature IL-18 in the skin, visual observation, or observation of skin tissue under a microscope, solely or in appropriate combination. Test substances whose effect of ameliorating atopic dermatitis have been confirmed through screening are useful as preventive and/or therapeutic drugs for atopic dermatitis.

EXAMPLES

The present invention will next be described in more detail by way of examples, which should not be construed as limiting the invention.

The test methods and materials employed in the Example described below are as follows:

(1) Northern Blotting

Murine caspase 1 (mCASP1) cDNA (Cell, 75, 653–660 (1993)) was procured from Osaka University (Dr. Miura). Total RNA, in its entirety, was obtained through extraction by use of an Isogen reagent (product of Nippon Gene Co., Ltd.) from tissues of CASP1 transgenic mice (KCASP1Tg) (obtained in Example 1 described hereinbelow) and control mice. In Northern blotting analysis, 10 μg of total RNA were size-fractionated by electrophoresis on 2% formaldehyde/agarose gels. RNA was transferred onto a nylon membrane (Immobilon-N, product of Millipore Co.) and probed with $^{32}$P-labeled cDNAs corresponding to human and murine CASP1 (regarding human CASP1 cDNA, see J. Dermatol. Sci., 21 (1994), 49–58). The RNA and cDNA were hybridized on the membrane. Subsequently, the blots on the membrane were washed twice with 1×SSC/0.1% SDS at 42° C., and twice with 2×SSC/0.1% SDS, and then exposed onto X-ray film at −70° C.

(2) Cytokines, Cytokine Assays, and Antibodies

Recombinant murine IL-1β (rmIL-1β) was purchased from R&D System. Human pro-IL-1β (hproIL-1β) was prepared in accordance with the method described in J. Exp. Med. 174: 821 (1991). Recombinant human IL-1β (rhIL-1β) and anti-human IL1β antibody were provided by Otsuka Pharmaceuticals. IL-1α level was measured by use of an ELISA kit (product of Endogen), and IL-1β and IFN-γ levels were measured by use of a kit manufactured by R&D System. Biological activities of IL-18 were determined through measurement of IFN-γ inducing activities by use of IL-18-responsive murine NK cells. Recombinant murine IL-18 (rmIL-18), rabbit neutralizing anti-murine IL-18 antibody and murine IL-18 ELISA kits were provided by Hayashibara Biochemical Laboratories. Use of the murine IL-18 ELISA kit permitted detection of IL-18 within a range of 10 to 1,000 pg/mL.

(3) Immunohistochemistry

Biopsy specimens obtained from transgenic mice and wild-type mice were fixed with phosphate-buffered formalin for two hours. Subsequently, the specimens were prepared for cutting of paraffin sections. The samples were immediately frozen in OCT compound (product of Miles) which is an embedding material for frozen tissues, and stored at −70° C. Cryostat sections (5 μm) were fixed with acetone for 5 minutes at 4° C. An appropriately diluted primary antibody was added to samples for incubation for one hour. After washing of the samples, the primary antibodies that had been bound were visualized by use of a Vectastein Elite kit (product of Vector Laboratories) with AEC (product of Dako Japan) as a substrate.

(4) Terminal Deoxynucleotidyl Transferase-mediated dUTP-Biotin Nick End Labeling (TUNEL)

DNA fragmentation of skin-biopsy specimens in paraffin sections were examined by TUNEL staining in accordance with the method described in Arch. Dermatol., 133: 845 (1997).

(5) Immunoblotting

Immunoblotting was performed in accordance with the method described in J. Clin. Invest. 87: 1066 (1991). DNA and RNA were removed by use of an Isogen kit. Epidermal cell lysates prepared from transgenic mice and control mice were individually suspended in SDS-sample buffer under reducing conditions. Then, the electrophoresed proteins were transferred onto a nitrocellulose membrane (product of Scheicher & Schuell) by use of a semi-dry blotter (product of Bio-Rad). A primary antibody was added to the membrane for incubation for one hour. Subsequently, alkaline-phosphatase-labeled anti-mouse IgG or anti-rabbit IgG was added to the membrane for secondary incubation. Finally, the samples were allowed to develop color with a Western Blue Substrate (product of Promega).

(6) Pro-IL-1β (proIL-1β) Processing Activity

Recombinant human pro-IL-1β (rhproIL-1β) was incubated along with fresh epidermal lysate for 10 to 30 minutes. SDS-sample buffer was added thereto, and the mixture was immediately boiled. The resultant samples were analyzed by immunoblotting by use of an anti-human IL-1β antibody and a Western Blue detection kit (product of Promega).

Example 1

(1) DNA Construct and Creation of a Transgenic Mice 1.4 kb cDNA encoding the entire coding region of hproCASP1 was ligated into human keratin 14 promoter (kindly offered by Dr. E. Fuchs, Chicago University; Nature, 374, 159–162 (1995)) and rabbit β-globin intron (kindly offered by Dr. Tanaka, Kyoto University; Nature, 374, 159–162 (1995)) by blunt-end ligation (in FIG. 1, "K14 promoter," "β-glob. Int.," "1.4 kb hproCASP1," and "K14 polyA" refer to human keratin 14 promoter, rabbit β-globin intron, 1.4 kb of human procaspase 1 cDNA, and human keratin 14 polyA, respectively). The thus-obtained DNA fragment was injected into fertilized eggs of C57BL/L6 mice (Charles River Japan, Inc.) through microinjection in accordance with the method described in Dev. Growth Differ., 39: 257 (1997).

(2) Verification of Over-Expression of hCASP1 in the Skin of Transgenic Mice

The offspring mice was screened for incorporation of the transgene by PCR and Southern blotting using DNA from the tail skin. Of a total of 96 newborn mice, four mice (male 3, female 1) were hCASP1 transgenic (hereinafter these mice will be abbreviated as KCASP1Tg). The KCASP1Tg were healthy when born, and grew normally thereafter. However, before 8-weeks of age, they were smaller than their wild-type littermates. After this point in time, KCASP1Tg manifested chronic active dermatitis. Of the three male KCASP1Tg, one was mated with wild-type females, and generated KCASP1Tg and wild-type offspring in an 1:1 male:female ratio. All experiments were performed on the line heterozygous for the transgene compared with non-transgenic or wild-type littermates.

(3) Skin Conditions

Under conditions in which no special pathogens were detected, from 8 weeks of age, the KCASP1Tg clearly began to manifest rodent dermatitis of medium degree in peripheral portions of their eyes, which developed rapidly to grave erosive dermatitis. From time to time, skin ulcers were observed. Within one to two weeks thereafter, these symptoms developed on the face, ears, neck, torso, and legs. Subsequently, re-epitheliation occurred, and lichenoid dermatitis was locally developed, with recurrence of erosion and ulcers. After 16 weeks, a plurality of foci of skin disease were formed, and the ears and eye lids were deformed. Hair on the face and extremities disappeared, only leaving integument accompanied by multiple scars.

Under an optical microscope, the epidermis of the KCASP1Tg did not exhibit particular histological changes up until 6 weeks of age. The thick epidermis surrounding the ulcerated lesions of the KCASP1Tg of 10 weeks of age presented psoriasis-like changes accompanying parakeratosis and dermatitis partially associated with acanthosis. The corium in the ulcerated sites was infiltrated with numerous monocytes. The keratinocytes in the lesion sites exhibited eosinophilic necrosis with nuclear condensation, which is indicative of apoptosis of keratinocytes. In fact, the nuclei of the cells present in the skin lesion sites containing many keratinocytes were stained positive by means of TUNEL staining, which is employed for identification in DNA fragmentation. In contrast, no TUNEL-positive keratinocytes were observed in the skin samples from control littermates.

High level hCASP1 was detected in thick epidermal tissue samples from KCASP1Tg. In contrast, samples from control mice tested negative. In order to investigate whether ulceration was attributed to the functional Fas ligand (Fas-L) induced by mature IL-18 processed from endogenous pro-IL-18 by exogenous hCASP1, Fas-L neutralizing antibody was administered to KCASP1Tg before they started to develop changes in the skin. Specifically, in accordance with the method described in J. Exp. Med., 182: 1777 (1995), Fas-L neutralizing antibody (1 mg; MFL1, kindly provided by Dr. Higaki, Juntendo University) was intraperitoneally injected to each KCASP1Tg every week from the 5th week to the 9th week, and conditions of skin ulceration were observed. However, intensive treatment with anti-Fas-L neutralizing antibody was useless, permitting skin ulcers to develop. Therefore, apoptosis of keratinocytes is suggested to be induced independent of the action of the Fas/Fas-L pathway. IL-18 did not induce apoptosis in any sample from the tested cell lines and tested primary culture cells. Moreover, keratinocyte-specific IL-1 α transgenic mice did not manifest apoptosis-related skin ulcers. This suggests that IL-1 β does not participate in apoptosis of skin cells of KCASP1Tg, although IL-1β has the same functions as IL-1α.

(4) Detection of Mature hCASP1 in Skin

Figure 2:
FIG. 2 shows the results of Northern blot analysis regarding expression of mRNA of hproCASP1 in various tissues from KCASP1Tg.

Presence of hproCASP1 mRNA in cells of ear epidermis, back epidermis, liver, kidney, colon, lung, brain, and spleen of KCASP1Tg were detected through Northern blotting (FIG. 2). As a result, 1.4 kb hproCASP1 mRNA was found only in epidermal cells from the ear and the back of KCASP1Tg, but not in other tissues (liver, kidney, colon, lung, brain, and spleen of KCASP1Tg). FIG. 2 shows the results of Northern blotting: lane 1: a sample obtained from a non-transgenic littermates, lanes 2–9: hproCASP1 mRNA in the ear epidermal tissue, back epidermal tissue, liver, kidney, colon, lung, brain, and spleen of KCASP1Tg.

Figure 3:
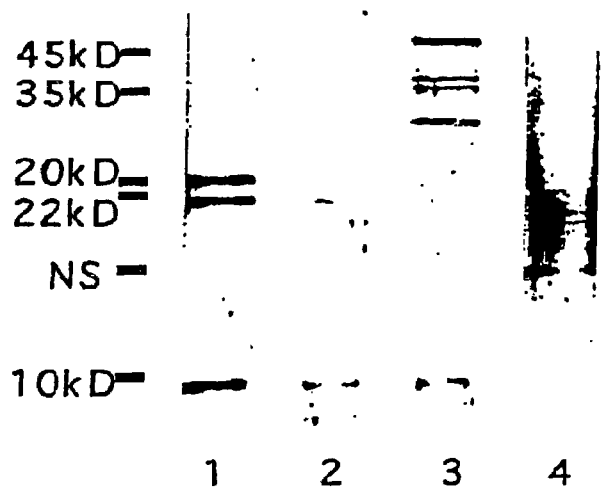
FIG. 3 shows the results of immunoblotting using anti-hCASP antibody for expression of hCASP1 protein in the skin of KCASP1Tg.

In order for caspase to exhibit its biological activities, proper processing is generally required. Pro-CASP1 has been reported to undergo autoproteolysis in vitro to thereby form mature CASP1 (Molecular Cell, 1:319 (1998); J. BIol. Chem., 271:13273 (1996)). The reports suggest that KCASP1Tg contains hCASP1 which has been spontaneously activated in the skin. In order to confirm this suggestion, the size of hCASP1 protein in KCASP1Tg skin lysate was measured by use of anti-hCASP1 antibody through immunoblotting (J. Biol. Chem., 271:13273 (1996)). As shown in FIG. 3, the skin lysate contained two activated components of hCASP1 (p20 and p10) and a precursor of p45, whereas the skin lysate from wild-type littermates contained no such component described above. These results reveal that hCASP1 in KCASP1Tg skin was spontaneously cleaved into mature form. In FIG. 3, lane 1: positive control THP-1 cells, lane 2: recombinant p20/p10 hCASP1, lane 3: KCASP1Tg skin lysate, lane 4: wild-type skin lysate.

Processing activity of hCASP1 in the skin of KCASP1Tg was measured by use of pro-IL-1β as a substrate in vitro. KCASP1Tg epidermal cell lysate was found to have produced 17 kD mature fragments through cleavage of 31 kD recombinant hproIL-1β. This cleavage was inhibited by a synthesized CASP1 inhibitor and iodoacetamide.

In addition, measurement was performed as to whether or not hCASP1 in the skin of KCASP1Tg exhibits biological activities in vitro. Since IL-1β and IL-18 were found to be constantly expressed in keratinocytes through experiments making use of mRNA, the size of each cytokine at the protein level in the skin was measured. Skin lysate from KCASP1Tg contained both mature IL-18 and mature IL-1β, whereas skin lysate from wild-type contained no such component. This is because transfected hCASP1 spontaneously cleaves endogenous precursor-type IL-1β and precursor-type IL-18 through spontaneous activation.

(5) IL-18 Level in Blood

Figure 4:
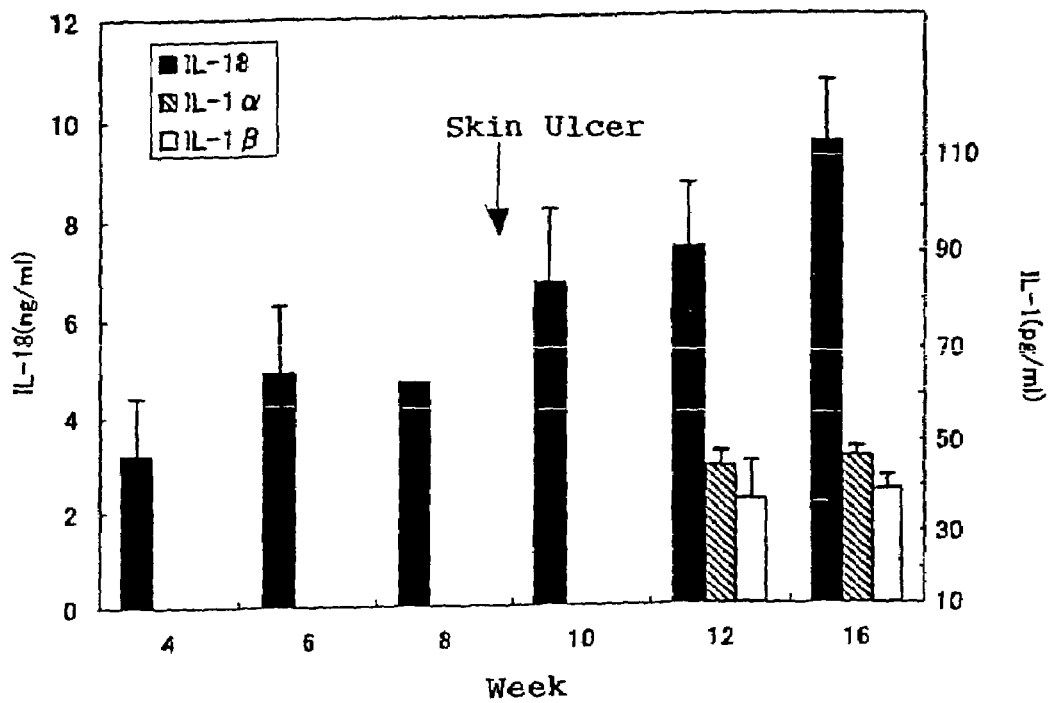
FIG. 4 shows concentrations of IL-18, IL-1β, and IL-1α in sera of KCASP1Tg.

Measurement was performed as to whether or not local activation of IL-18 and IL-1β by exogenous hCASP1 induces systemic accumulation of individual mature cytokines. FIG. 4 shows a high serum IL-18 level in KCASP1Tg of four weeks of age, which is statistically significant. The serum IL-18 level in wild-type littermates remained low (0.1 ng/mL or less) throughout the living period. The serum concentration of IL-18 in KCASP1Tgs gradually increased with growth. Only a small amount of IL-1β in KCASP1Tg serum was detected from the age of 12 weeks, whereas no IL-1β was detected in wild-type. Over-expression of hCASP1 in keratinocytes selectively elevated serum concentration of IL-18 rather than IL-1β.

In order to verify that serum IL-18 of KCASP1Tg is mature IL-18, biological activities of KCASP1Tg serum IL-18 were investigated. As a result, serum from KCASP1Tg was found to have ability to stimulate IL-18-responsive cloned natural killer cells to produce IFN-γ. Moreover, the ability to induce IFN-γ was completely inhibited by anti-IL-18 antibody (neutralizing antibody). This indicates that the serum from a KCASP1Tg contains active IL-18. However, IFN-γ was not detected in serum from a KCASP1Tg in a normal state. Thus, KCASP1Tg continuously secreted mature IL-18 into circulating blood.

(6) Skin Scratching Behavior of Transgenic Mice

Incidence of skin scratching behavior of KCASP1Tgs and healthy mice (C57BL/L6 mice) was measured for 40 minutes by visual observation.

Figure 5:
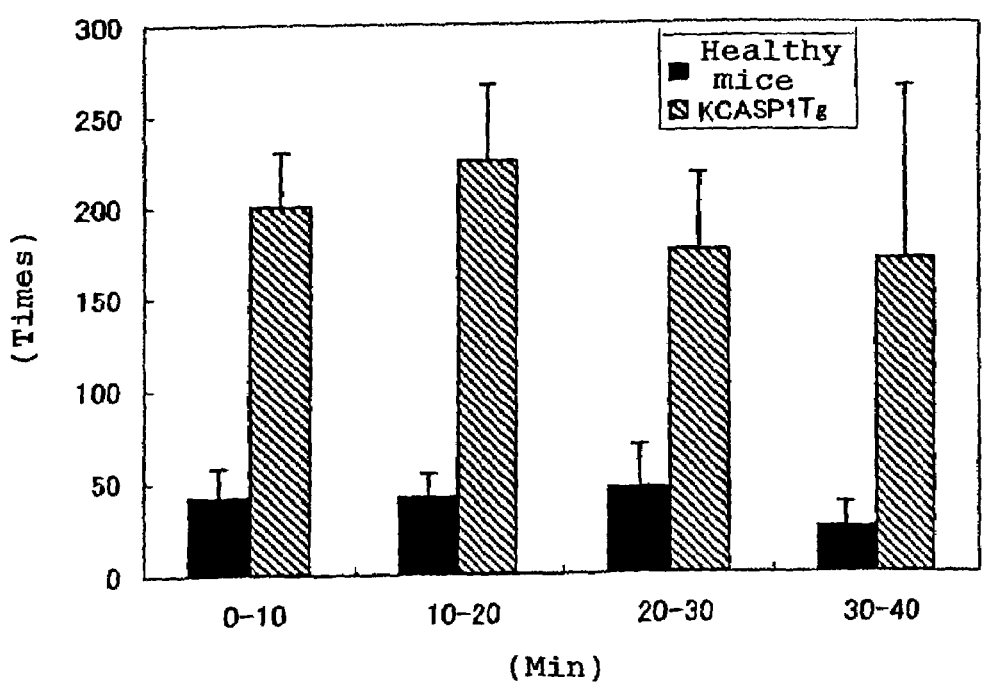
FIG. 5 shows the frequency of skin scratching of KCASP1Tg and healthy mice.

As a result, as shown in FIG. 5, healthy mice scratched their skin 50 times or less per 10 minutes, whereas KCASP1Tgs scratched 200 times or more times per 10 minutes, thereby demonstrating production of severe examthemata accompanying itchiness.

(7) Blood IgE Level and Blood Histamine Level

Figure 6:
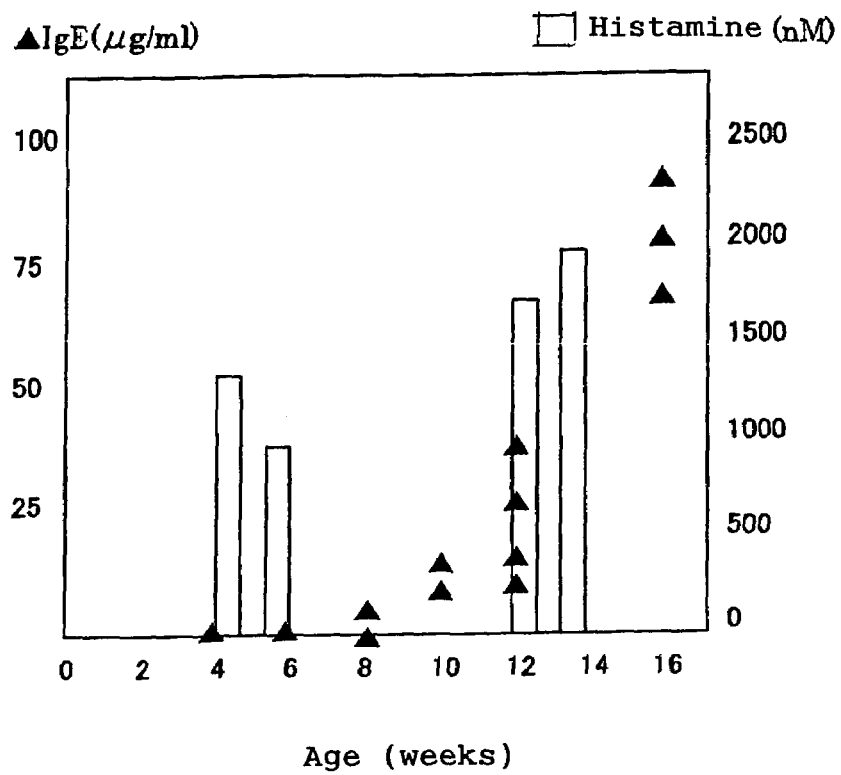
FIG. 6 shows time-course changes in blood IgE and histamine levels of KCASP1Tg.
Figure 7:
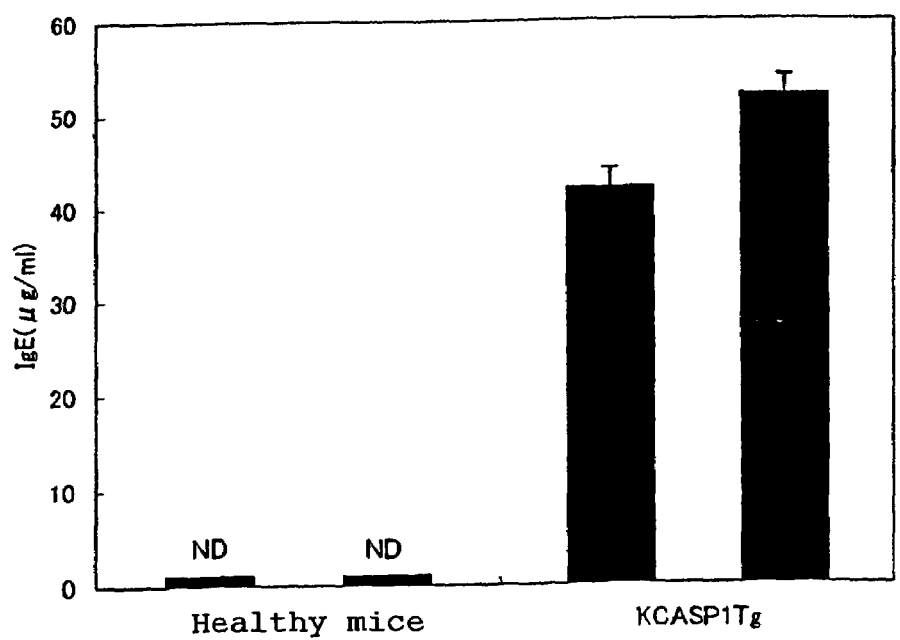
FIG. 7 shows blood IgE levels of 14-week-old KCASP1Tg and healthy mice.

Blood IgE level (RIA method) and blood histamine level (ELISA method) of KCASP1Tgs were measured with time. The results are shown in FIG. 6. Blood IgE level of KCASP1Tg (14 weeks of age) and healthy mice was measured, and the results are shown in FIG. 7. These results show that the blood histamine level of the transgenic mice of the present invention has elevated as high as 2,000 nM at 13 to 14 weeks of age, whereas blood IgE level has also elevated extremely high; i.e., not less than 50 μg/mm at 16 weeks of age.

Industrial Applicability

Since the transgenic non-human mammals of the present invention spontaneously develop atopic dermatitis in the absence of specific pathogenic microorganisms, they are useful as disease model animals. Use of transgenic animals of the present invention enables development of preventive/therapeutic drugs for atopic dermatitis on the mechanism of natural immunity, and elucidation of the onset mechanism of atopic diseases.

What is claimed is:

1. A transgenic mouse or an offspring thereof,
comprising an exogenous caspase 1 gene encoding caspase 1 in somatic cells and germ cells of the transgenic mouse, and wherein the caspase 1 gene is expressed specifically in the skin; and,
wherein the mouse or the offspring exhibits the phenotype of exhibiting at least one symptom of atopic dermatitis selected from the group consisting of erosive dermatitis, skin ulcer, and erosion.

2. The transgenic mouse of claim 1, wherein the DNA comprising an exogenous caspase 1 gene encoding caspase 1 further comprises a promoter for a skin-specific protein.

3. The transgenic mouse of claim 2, wherein the promoter for a skin specific protein comprises a promoter for keratin.

4. The transgenic mouse of claim 2, which continuously secretes mature IL-18 into the blood.

5. The transgenic mouse of claim 1, wherein the exogenous caspase 1 gene encodes human caspase 1.

6. The transgenic mouse of claim 1, wherein the exogenous caspase 1 gene encodes murine caspase 1.

7. The transgenic mouse of claim 1, which continuously develops atopic dermatitis.

8. The transgenic mouse of claim 1, wherein the phenotype is erosive dermatitis.

9. The transgenic mouse of claim 1, wherein the phenotype is a skin ulcer.

10. A screening method for identifying a substance that can prevent or treat atopic dermatitis comprising
administering the substance to the transgenic mouse of claim 1, and determining whether a symptom of atopic dermatitis is ameliorated or prevented,
wherein if the substance ameliorates or prevents a symptom of atopic dermatitis in the transgenic mouse then the substance can be used to prevent or treat atopic dermatitis.

11. The method of claim 10, wherein determining whether a symptom of atopic dermatitis has been ameliorated or prevented comprises measuring the level of mature IL-18 in the blood, detecting mature IL-18 in the skin, visual observation, microscopic observation of skin tissue, or measuring the histamine level in the blood.

12. A method for making the transgenic mouse of claim 1, comprising
introducing a DNA comprising an exogenous caspase 1 gene that will express caspase 1 specifically in the skin of the mouse into a fertilized egg of a mouse, and
implanting the fertilized egg comprising the DNA into a female mouse, wherein the fertilized egg develops into the transgenic mouse.

\* \* \* \* \*